United States Patent [19]
Yelderman et al.

[11] Patent Number: 5,067,492
[45] Date of Patent: Nov. 26, 1991

[54] DISPOSABLE AIRWAY ADAPTER

[75] Inventors: Mark Yelderman, Plano, Tex.; Daniel S. Goldberger, San Francisco; James R. Braig, Oakland, both of Calif.

[73] Assignee: Critikon, Inc., Tampa, Fla.

[21] Appl. No.: 564,179

[22] Filed: Aug. 7, 1990

[51] Int. Cl.$^5$ .............................................. A61B 5/08
[52] U.S. Cl. ................................ 128/719; 128/204.23
[58] Field of Search ............ 128/719, 716, 724, 204.22, 128/204.23, 664; 250/343; 156/215

[56] References Cited

U.S. PATENT DOCUMENTS

| | | | |
|---|---|---|---|
| 3,727,050 | 4/1973 | Kerr | 250/343 |
| 3,987,303 | 10/1976 | Stoft et al. | 250/343 |
| 4,287,750 | 9/1981 | Eckstein et al. | 73/1 G |
| 4,581,942 | 4/1986 | Ogura et al. | 73/861.28 |
| 4,648,396 | 3/1987 | Raemer | 128/204.22 |
| 4,662,360 | 5/1987 | O'Hara et al. | 128/9 |
| 4,727,886 | 3/1988 | Conrardy et al. | 128/725 |
| 4,772,790 | 9/1988 | Aldridge | 250/343 |
| 4,810,924 | 3/1989 | Jelic | 313/609 |
| 4,811,327 | 3/1989 | Petrov et al. | 369/111 |

FOREIGN PATENT DOCUMENTS

2923301 12/1980 Fed. Rep. of Germany ...... 128/716

OTHER PUBLICATIONS

"A Reliable, Accurate CO$_2$ Analyzer for Medical Use", Rodney J. Solomon, Hewlett-Packard Journal, Sep. 1981, pp. 3-21.

Primary Examiner—Edgar S. Burr
Assistant Examiner—Stephen R. Funk
Attorney, Agent, or Firm—Woodcock Washburn Kurtz Mackiewicz & Norris

[57] ABSTRACT

A disposable endotracheal airway adapter for use in proximity of a patient's mouth in the measurement of the concentraton of respiratory gases. The disposable airway adapter of the invention provides a conduit for patient respiratory gases and allows the passage of infrared radiation through the gases for measuring the constituent concentration of the respiratory gases while keeping the patient gases from coming in contact with the analyzer mechanism. The body of the airway adapter is designed to connect in series with the airway tubing which connects a patient to a mechanical respirator or anesthesia breathing circuit. The body of the airway adapter is very light in weight and is formed of inexpensive material such as polyethylene or polypropylene so that it may be manufactured inexpensively and discarded after each use. An inexpensive optical window in the adapter is also formed of material such as polyethylene or polypropylene so that the gas analyzer can pass light into the sample for analysis. Preferably, the optical windows of the invention are made of the same material as the adapter body. Since the adapter of the invention may be disposed of after use on a single patient, sterilization expenses and cross-contamination may be minimized. Also, calibrating integrity is maintained through a calibration process which accounts for the non-linearity of the absorption spectra of the window material in the region of interest.

6 Claims, 3 Drawing Sheets

DISPOSABLE AIRWAY ADAPTER

BACKGROUND OF THE INVENTION

1. Field of the Invention

The present invention relates to a device which provides a conduit for patient respiratory gases and allows the passage of infrared radiation from a gas analyzer through the gases, and more particularly, to a disposable airway adapter for use with a respiratory gas analyzer.

2. Brief Description of the Prior Art

Respiratory gas analyzers function by passing light of a specific wavelength (typically infrared) through a gas and measuring the amount of light that is absorbed. Such a respiratory gas analyzer is disclosed by Solomon in an article entitled "A Reliable, Accurate $CO_2$ Analyzer For Medical Use," *Hewlett-Packard Journal*, September 1981, Pages 3–21, for example. Solomon therein describes the HP $CO_2$ Analyzer Model 47210A Capnometer, which measures the amount of carbon dioxide in a patient's breath for medical diagnostic purposes. The HP Model 47210A Capnometer is comprised of an airway adapter, a sensor and a processor box. The airway adapter, a hollow aluminum casting with sapphire windows, is inserted in series with the ventilator plumbing and is used to keep the patient's respiratory gases from coming in contact with the sensor mechanism. The sensor is snapped over the airway adapter windows, and the measurement is made directly on the artificial airway through which the patient is breathing. The sensor contains all the optical components necessary to make the infrared measurement and is connected to the processor box by a cable. The processor box powers the sensor, processes the return signal, and presents the data via an LED display.

Solomon states that the sensor of the HP Model 47210A Capnometer must be small, rugged, light-weight, and easily cleaned, and that the sensor must help isolate the processor box from any high voltages caused by the use of defibrillation equipment. The airway adapter also must be rugged and light-weight. It must be sterilizable and the infrared path length must be stable and consistent from unit to unit to minimize the total system error. Mating the airway adapter to standard ventilation plumbing also must be simple and reliable. In fact, the airway adapter of the HP Model 47210A Capnometer must satisfy a number of critical requirements. For example, sterilizability, a stable infrared path length and ruggedness dictate a series of materials requirements. Moreover, since measurement accuracy is directly related to the infrared path length through the sample, any variation from the nominal 3-mm gap results in an error proportional to the difference in the gap from the nominal value. Thus, to achieve the required stability in view of the other requirements, the airway adapter of the HP Model 47210A Capnometer is made of aluminum.

Aluminum is a preferred material for the airway adapter of the HP Model 47210A Capnometer since aluminum can withstand sufficiently high temperatures to allow sterilization of the airway adapter The aluminum airway adapter of the HP Model 47210A Capnometer also has two sapphire windows that are epoxy bonded to each side of the aluminum gas passage such that the gap between the windows forms a precise path length for the gas sample. The gap is set to a desired value during assembly by placing a shim of the correct thickness between the two windows and firmly clamping the windows to the shim while the epoxy bond cures, thereby forming the gap.

An airway adapter so formed allows accurate $CO_2$ readings to be made for diagnostic purposes. However, as noted above, the HP Model 47210A Capnometer is made of investment cast aluminum while the windows are made of polished sapphire disks. The resulting adapter is thus too expensive to be disposable and hence must be sterilizable for multiple patient uses. A less expensive, and hence disposable, airway adapter is desired which maintains comparable accuracy in measurement.

It is generally known that medical devices may be made disposable for sanitary purposes by forming the devices of plastics such as polypropylene or polyethylene. For example, O'Hara, et al. disclose in U.S. Pat. No. 4,662,360 a disposable speculum which functions as a sanitary protective cover or sheath for an ear canal probe of a tympanic thermometer for measuring temperature using infrared energy. In particular, O'Hara, et al. disclose that polypropylene and polyethylene may be used as an infrared transparent membrane since both plastic materials are substantially transparent to infrared radiation at the wavelengths necessary for the infrared temperature measurement. Such an infrared transparent membrane must be relatively thin to minimize the attenuation of infrared radiation passing therethrough so that a thermopile or other detector receiving infrared radiation through the membrane will sense the maximum amount of infrared radiation available. The membrane should also have a uniform thickness, with no wrinkles or other structural characteristics that will distort the infrared radiation passing therethrough, for such distortion can introduce errors in the temperature measurement process. Accordingly, the membrane in O'Hara et al's preferred embodiment of a disposable speculum serving as an infrared window is made of polypropylene or polyethylene film having a thickness in the range of 0.0005 to 0.001 inch. Preferably, the speculum also mates with the probe of the tympanic thermometer so that the membrane is stretched tightly over the probe tip, thereby removing any wrinkles in the membrane.

O'Hara, et al. also disclose that the speculum is preferably manufactured by injection molding the entire speculum in one integral piece. However, since it is difficult to integrally mold the entire speculum with the walls and the membrane having thicknesses in the desired ranges, O'Hara, et al. disclose a preferred method of fabrication including injection molding of the tubular body portion of the speculum and then affixing a separate membrane to the frontal end of the body portion. A portion of the film defining the membrane thus is severed from a larger film and thermally bonded to the tubular body portion. This technique is relatively inexpensive and is conducive to mass production.

Thus, the device of O'Hara, et al. contains a thin infrared transmitting window for the altogether different application of measuring temperature via non-contact thermometry. Namely, the O'Hara, et al. device is. used for separating the sensor probe of a tympanic thermometer from a patient's ear while taking temperatures. This device is manufactured by melt welding a thin polypropylene or polyethylene film onto a molded polypropylene or polyethylene body piece. Accordingly, although the resulting disposable speculum may be manufactured quite inexpensively, the device of O'-

Hara, et al. does not meet the structural requirements noted by Solomon for the manufacture of an airway adapter for use with a respiratory gas analyzer.

Raemer discloses in U.S. Pat. No. 4,648,396 a respiration detector having an infrared source and detector pair disposed on opposite sides of a cuvette through which the gas stream inhaled and exhaled by a patient is passed. The amount of $CO_2$ in the exhaled stream is compared with that in the inhaled stream. Where the difference is greater than a predetermined amount, a breath is determined to have been detected, thus avoiding the necessity of calibrating the apparatus against any absolute reference standard. In a preferred embodiment of the respiration detector of Raemer, the elements of the sensor assembly are enclosed in a molded plastic housing with plastic windows. The gas cuvette also comprises plastic windows, preferably formed integrally, of a material which is relatively transparent to infrared radiation, such as polycarbonate plastics. In other words, Raemer specifies that both the sensor assembly and the cuvette have plastic windows. However, since the device of Raemer merely functions to determine whether the patient is breathing and not to determine absolute concentrations of constituents in the exhaled gases, measurement accuracy and hence calibration is not necessary. In fact, the Y-shaped adapter device of Raemer is disposed too far away from the patient's mouth to allow quantitative readings for determining the concentration of constituents in the exhaled air. Thus, the adapter device of Raemer, although plastic, could not function as a disposable airway adapter for use with a respiratory gas analyzer.

Accordingly, the inventors of the present invention know of no suitable prior art disposable airway adapter and believe there is a need in the art for an airway adapter for use with an infrared-type respiratory gas analyzer whereby the airway adapter has the suitable optical properties for allowing the infrared energy to pass through the gases yet is not prohibitively expensive. Preferably, such a device would be inexpensive enough that it may be disposable and hence need not be repeatedly sterilized to prevent the spread of disease and the like. The present invention has been designed to meet these needs.

SUMMARY OF THE INVENTION

The present invention provides a disposable airway adapter which overcomes the above-mentioned problems in the prior art and also eliminates the pumps and water traps found in conventional sidestream analyzers. The airway adapter of the invention is preferably used with a detector system such as that described in related U.S. application Ser. No. 07/522,208, which eliminates the need for a modulated or "chopped" infrared beam so as to simplify the sensor system. The exceptional stability of such a detector system prevents the operator from having to calibrate or zero the detector between uses and also enables a disposable airway adapter of the type herein disclosed to be used without sacrificing accuracy in measurement. Moreover, since the optical characteristics of the airway adapter of the invention are calibrated during manufacturing, the introduction of the airway adapter into the path of the infrared light does not require extra calibration steps to be taken by the user. The present invention thus provides a simple, low cost alternative to the prior art devices.

In particular, the present invention relates to a disposable airway adapter for use in proximity of a patient's mouth in the measurement of the concentration of respiratory gases. A preferred embodiment of the invention comprises a substantially tubular portion formed of at least one of polypropylene and polyethylene, the tubular portion having oppositely disposed openings in a cross-sectional direction thereof, and at least two windows formed of a thin layer of at least one of polypropylene and polyethylene. Preferably, the windows are disposed in the openings of the tubular portion so as to be a predetermined distance from each other. The windows also separate an inside portion of the tubular portion from measuring means for measuring the concentration of respiratory gases. The measuring means is calibrated in the openings so as to compensate for differential absorption effects caused by the different constituents and the relative positions of the windows with respect to each other. The resulting device thefore need not be calibrated by the user.

In accordance with an aspect of the invention, the tubular portion includes snap-fit means for enabling the airway adapter to snap-fit into a housing of the measuring means. In addition, the thin layer also preferably has a thickness of approximately 0.005 inch. Also, the aforementioned predetermined distance is approximately 0.3 inch in a preferred embodiment.

The invention also includes a method of manufacturing a disposable endotracheal airway adapter for use in proximity of a patient's mouth in the measurement of the concentration of respiratory gases comprising the steps of:

forming a substantially tubular portion of at least one of polypropylene and polyethylene, the tubular portion having oppositely disposed openings in a cross-sectional direction thereof;

forming at least two windows of a thin layer of at least one of polypropylene and polyethylene;

disposing the windows in the openings of the tubular portion so as to be a predetermined distance from each other; and adhering the windows to the tubular portion so as to cover the openings.

The manufacturing method of the invention may also include the further steps of determining an infrared absorption fingerprint of each of the windows and compensating for differential absorption effects of each window. In this manner, the windows of each adapter may be made interchangeable. In addition, in a preferred method, the adhering step comprises the steps of cutting a drum band, attaching the drum band to the periphery of the thin layer, and heat staking the drum band and thin layer to the tubular portion over the openings. Of course, other suitable adhering techniques may also be used in accordance with the invention. Moreover, the adapter may be injection molded as a complete part at one time if means are provided for forming the optical window therein.

BRIEF DESCRIPTION OF THE DRAWINGS

The objects and advantages of the invention will become more apparent and more readily appreciated from the following detailed description of presently preferred exemplary embodiments of the invention taken in conjunction with the accompanying drawings of which.

DETAILED DESCRIPTION OF PRESENTLY PREFERRED EMBODIMENTS

A disposable airway adapter with the above-mentioned beneficial features in accordance with presently preferred exemplary embodiments of the invention will be described with reference to FIGS. 1-3. It will be appreciated by those of ordinary skill in the art that the description given herein with respect to those figures is for exemplary purposes only and is not intended in any way to limit the scope of the invention. All questions regarding the scope of the invention may be resolved by referring to the appended claims.

The present invention relates to a disposable airway adapter which is used to keep the patient gases being monitored from coming in contact with the respiratory gas analyzer mechanism. The body of the device of the invention is designed to connect in series with the tubing used to connect a patient to a mechanical respirator or anesthesia breathing circuit. The disposable airway adapter body is preferably very light-weight so that it does not interfere with the breathing tube which is usually inserted into the patient's trachea. In addition to being a gas conduit, the airway adapter of the invention provides an optical window through which the gas analyzer can pass light onto the sample for analysis. One key property of the optical windows used in the disposable airway adapter of the invention is that they are low in cost. They are preferably made of the same material and molded as part of the body of the adapter using a manufacturing process as described below. The low cost windows and low cost plastic body of this device allow it to be disposed of after use on a single patient. Such single patient use saves sterilization expenses and eliminates cross-contamination. This is especially useful with highly contagious diseases such as Tuberculosis, but is also a benefit in routine cases where unknown diseases may be carried but not active. Also, since the airway adapter of the invention is relatively small and light in weight, it may be placed close to the patient's mouth so as to allow quantitative readings for purposes of determining the concentrations of the constituents in the expired air.

Figure 1B:
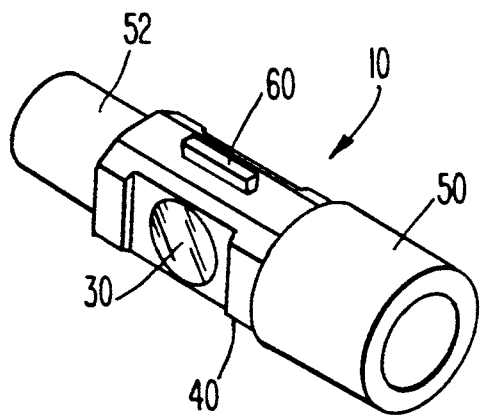
FIG. 1B illustrates a perspective view of a disposable airway adapter body having optical windows in accordance with the invention.
Figure 1A:
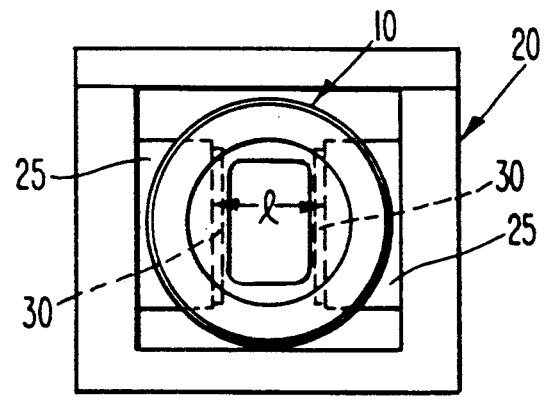
FIG. 1A illustrates an end view of a disposable airway adapter in accordance with the invention which is snap-fit into the housing of an infrared gas analyzer.

The disposable airway adapter in accordance with the invention is shown by way of example in FIGS. 1A and 1B. As shown in FIG. 1A, the disposable airway adapter 10 of the invention is preferably snap-fit into the housing 20 of a gas analyzer 1 25 of the type described by the present inventors in related U.S. patent application Ser. No. 07/522,208 entitled "Shutterless Optically Stabilized Capnograph", filed May 11, 1990, the contents of which are hereby incorporated by reference in their entirety as if set forth fully herein. As shown, portions of the gas analyzer housing 20 protrude and slightly "squeeze" the optical windows 30 of the adapter body 40 so as to accurately locate the optical windows 30 in place in front of the detectors of the gas analyzer 25 so that the membranes of the optical windows 30 are a predetermined distance 1 from each other. This "optical path length," 1, is maintained precisely by the rigid housing 20 of the gas analyzer 25 without requiring precision and strength of the airway adapter 10. The present invention is thus characterized in that the optical path length is maintained by the durable gas analyzer, not the disposable airway adapter per se. A perspective view of the airway adapter 10 showing the adapter body 40 and the optical windows 30 in accordance with the invention is shown in FIG. 1B.

The optical windows 30 and the airway adapter body 40 of the airway adapter 10 in accordance with the invention are formed of plastic, preferably polyethylene and polypropylene. The plastic and the shapes used in forming the airway adapter 10 of the invention render it slightly deformable such that when the adapter is placed in connection with the gas analyzer 25 the adapter assumes or conforms to the shape of the gas analyzer housing 20, particularly the window to window spacing. As noted above, the spacing between entry and exit windows is critical to the proper operation of the gas analyzer 25, and accordingly, this distance is referred to herein as the "optical path length" of the gas analyzer 25. In the HP Model 47210A Capnometer device described above, this "optical path length" is controlled by the rigidity of the adapter body and the precision placement of the sapphire windows during assembly. By contrast, in the present invention the "optical path length" is controlled by the gas analyzer 25, which presses the pliable adapter body 40 into shape when the adapter is installed into the gas analyzer's housing 20 as shown in FIG. 1A. In other words, the airway adapter 10 in accordance with the invention is designed such that it conforms to the housing 20 of the gas analyzer 25 so that a precision "optical path length" 1 may be maintained even when less expensive materials such as plastic are used for forming the airway adapter 10. This leads to the disposable nature of the invention.

The airway adapter 10 of the invention consists of a single piece molded plastic part (adapter body) 40 which is preferably made of polyethylene or polypropylene. Differing views of a preferred embodiment of such a device are shown by way of example in FIGS. 2A-2I.

Figure 2A:
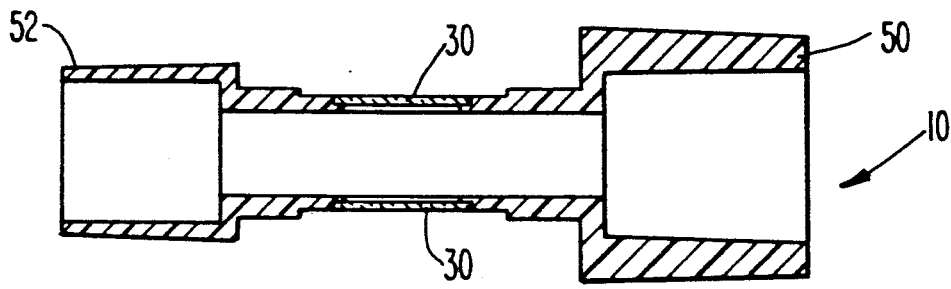
FIG. 2A illustrates a top-view of an embodiment of a disposable airway adapter in accordance with the invention.

FIG. 2A shows a top-view of a disposable airway adapter body 40 in accordance with a preferred embodiment of the invention. As shown, the airway adapter body 40 has connecting portions 50 for connecting the airway adapter 10 to respective airway tubes from the patient. The connecting portions 50 and 52 are sufficiently tapered so as to form standard conical fittings. The airway adapter body 40 also includes windows 30 which are spaced at a predetermined optimum "optical path length" distance (1) from each other, preferably 0.340 inch, as shown.

Figure 2B:
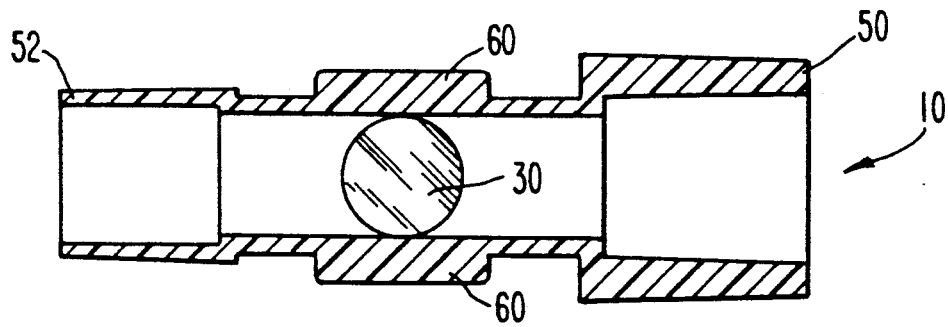
FIG. 2B illustrates a side-view of the disposable airway adapter of FIG. 2A.
Figure 2C:
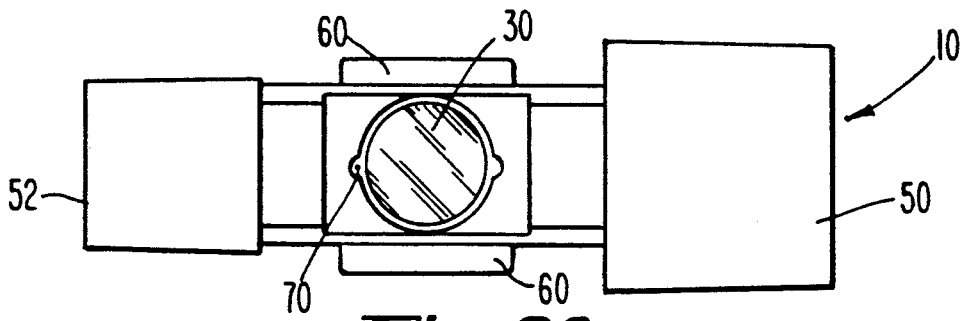
FIG. 2C illustrates a side-view of an exemplary exterior configuration of a disposable airway adapter in accordance with the invention.

FIG. 2B shows a side-view of the airway adapter body 40 showing a window 30 and snap-fitting flanges 60. FIG. 2C shows a more detailed view of the airway adapter body 40. As shown, the periphery of the window 30 may include a ring portion 70 at which the window 30 may be adhered to the adapter body 40 as will be described below.

Figure 2F:
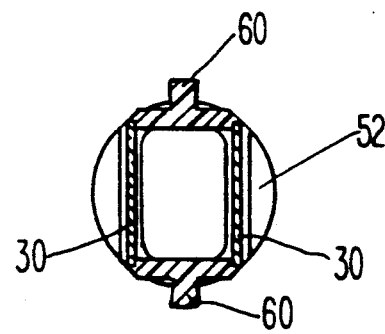
FIGS. 2E-2G illustrate different cross-sectional and end views of the disposable airway adapter of FIGS. 2A-2D of the invention.
Figure 2D:
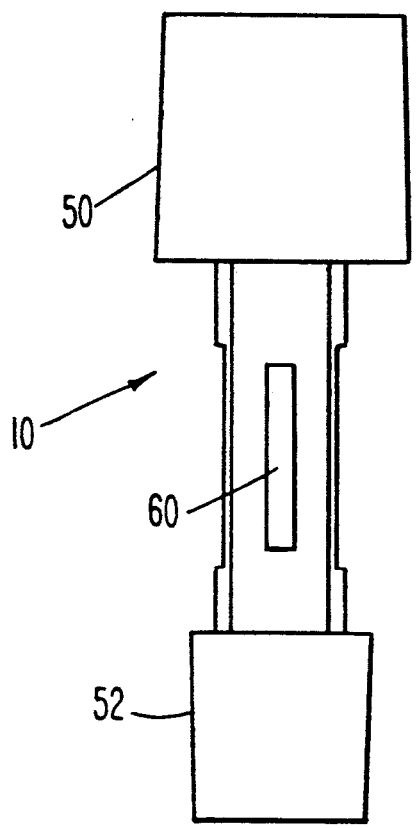
FIG. 2D illustrates a top-view of an exemplary exterior configuration of a disposable airway adapter in accordance with the invention.
Figure 2G:
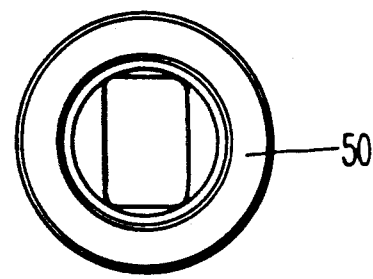
Figure 2E:
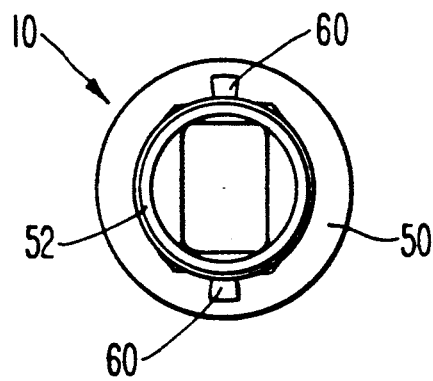
Figure 2H:
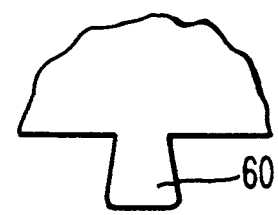
FIGS. 2H and 2I illustrate alternative embodiments of a snap-fitting flange for use on the disposable airway adapter in accordance with the invention.
Figure 2I:
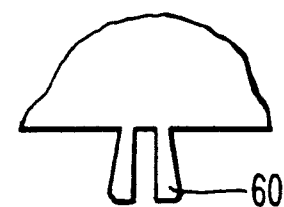

FIG. 2D shows a top-view of the airway adapter body 40 with its snap-fitting feature 60. FIG. 2E shows an end view of the airway adapter body 40 of FIGS. 2C and 2D at the left portion thereof, while FIG. 2F shows a cross-sectional view of the airway adapter body 40 through lines C—C as shown in FIG. 2C. FIG. 2G shows an end view of the airway adapter body 40 of FIGS. 2C and 2D at the right portion thereof. Finally, FIGS. 2H and 2I show alternative embodiments of the snap-fitting feature 60 in accordance with the invention.

As noted above, the disposable airway adapter body 40 of FIG. 2 may be constructed of a single piece molded plastic part, preferably made of polyethylene or polypropylene. A preferred embodiment of the optical windows 30 of the invention may be formed of plastic materials such as Kynar ® (available from ATOCHEM Corp.) Such materials are preferably used since they are inexpensive, transparent to infrared energy and rigid, yet are not susceptible to moisture condensation.

Moisture condensation on infrared windows has been a problem in prior art devices. The resulting fog absorbs some unknown portion of the infrared energy and affects the analyzer measurements. The fog is created when warm, moist gases inside the respiratory circuit react with cooler optical windows of the airway adapter. As noted above, prior art devices use sapphire as the window material, which has a relatively high mass and high heat capacity. By contrast, the thin plastic windows of the invention are very low in mass and have a low heat capacity. Such windows can reach an equilibrium temperature with the respiratory gases very quickly. Due to the resulting lack of temperature differential, moisture will not condense onto the windows, thereby avoiding the measurement inaccuracies caused by moisture condensation.

The airway adapter 10 of the invention is preferably manufactured using a two-piece assembly. This is currently desirable because tooling for a mold capable of producing thin enough window sections 30 to allow sufficient passage of infrared light is expensive. Such thin window sections are necessary because if the optical windows are too thick, they will absorb too much energy and render the analyzer 25 inoperative. To overcome this problem, the present invention is preferably fabricated by forming a thin membrane for use as the optical window 30 and then adhering it over the openings in the airway adapter body 40. The thin layer which forms the optical windows 30 is preferably placed on a drum head and then adhered to the adapter body 40 over the opening for the windows 30. In other words, the manufacturing process comprises the steps of molding the airway adapter body 40, cutting a drum band which fits into portion 70 shown in FIG. 2C, forming the thin optical window 30 sections, and adhering the optical window 30 to the airway adapter body 40 by heat pressing the window 30 periphery about the drum band by heat staking or by adhering the window 30 to the adapter body by some other acceptable adhering technique. In a preferred embodiment, the airway adapter body 40 is preferably formed by injection molding while the adhering is preferably done through ultrasonic bonding, inertial welding or by using a suitable adhesive. In addition, to insure sufficient optical quality using this technique, the windows 30 are preferably formed to be 0.005±0.001 inch thick. This thickness represents an acceptable trade-off between mechanical integrity and light absorption capabilities. As a result, the airway adapter of the invention may be manufactured very inexpensively while remaining structurally strong.

The optical transmission of the sapphire windows used in the HP Model 47210A Capnometer is "flat" in the region of interest. This allows the HP Model 47210A Capnometer to be calibrated without the windows in place and assures that the installation of the adapter containing sapphire windows will not affect the instrument's calibration. The optical transmission of the material used in the present invention (preferably polyethylene or polypropylene), on the other hand, is not flat within the region of interest. Since each window is not spectrally flat, "differential absorption" effects may adversely affect the resulting analyzer readings. Accordingly, to accommodate this "differential absorption" the gas analyzer 25 in accordance with the present invention is calibrated with a representative sample of the windows 30 in place at the completion of the manufacturing process. When thus calibrated, the effect of the component materials of the windows 30 is taken into account and the gas analyzer 25 is able to operate accurately with the airway adapter 10 in place for normal use. This calibration is done at the factory and is of no burden to the user.

Figure 3:
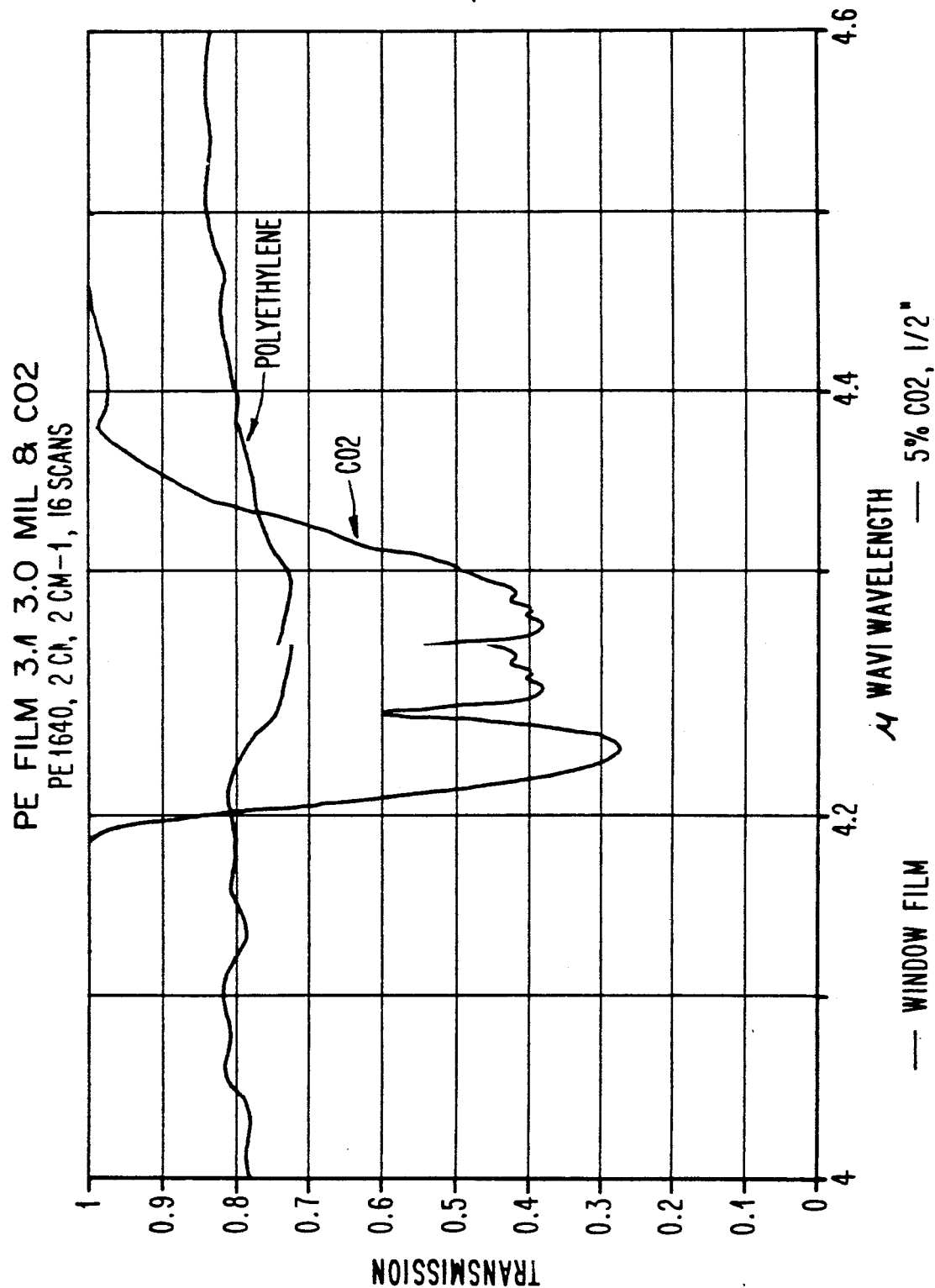
FIG. 3 illustrates an absorption spectrum in the region of interest for polyethylene and $CO_2$ gas.

FIG. 3 illustrates the absorption spectrum in the region of interest of polyethylene and $CO_2$ gas. As just described, FIG. 3 illustrates that the spectrum for polyethylene used in the windows 30 is not spectrally "flat" and thus must be accommodated in the calibration of the analyzer for accurate readings to result. This calibration is necessary in accordance with the invention, for in the production of disposable adapters it is critical that each window 30 have the same infrared absorption spectrum in the region of interest so that all windows 30 are functionally interchangeable. The airway adapter 10 of the present invention is thus preferably used with a gas analyzer 25 which has been designed so as to relax the optical requirements on the windows 30. Such an optical analyzer is disclosed, for example, in related U.S. patent application Ser. No. 07/522,202 entitled "Optically Stabilized Infrared Capnograph" by the present inventors, where a reference channel is used so as to allow the airway adapters to have different average transmissions, such as that which might arise from different window thicknesses. The requirement that remains is that each window 30 has identical absorption spectra in the wavelengths of interest, which is controlled by the chemical composition of the material used to form the window. During manufacture, the windows are constrained in the apertures of the airway adapter body 40 during bonding so as to remain flat. Anti-reflection coatings are also preferably placed on the thin films so as to avoid reflection of the infrared light.

Although exemplary embodiments of the invention have been described in detail above, those skilled in the art will readily appreciate that many additional modifications are possible in the exemplary embodiments without materially departing from the novel teachings and advantages of the invention. For example, the manufacturing process for the airway adapter 10 of the invention may be modified such that following the initial molding of the airway adapter body 40 a "hot stamping" operation is performed which details the optical window sections by squeezing them thinner and flatter between two heated surfaces that are polished to optical quality. The result is a clear, thin optical window 30 which is inherently part of the adapter body 40. The resulting airway adapter 10 is thus formed of only a single piece and is accordingly structurally stronger and less expensive. Accordingly, these and all such modifications are intended to be included within the scope of this invention as defined in the following claims.

What is claimed is:

1. An endotracheal airway adapter for single patient use in proximity of a patient's mouth during quantitative measurement of the concentration of respiratory gases of the patient by a respiratory gas analyzer having infrared transmission and detection means and means for housing said infrared transmission and detection means, said airway adapter comprising:

a substantially tubular plastic portion made of material which is slightly deformable and having oppositely disposed openings in a width-wise direction thereof;

at least two windows formed of a thin layer of plastic, said windows being disposed in said openings of said tubular plastic portion so as to be a predetermined distance from each other during measurement of said concentration of respiratory gases by said infrared transmission and detection means of said respiratory gas analyzer; and means for positioning said tubular plastic portion in said housing means of said respiratory gas analyzer such that said tubular plastic portion is slightly deformed to thereby dispose and maintain said windows in a predetermined spaced configuration between said infrared transmission and detection means during measurement of said concentration of respiratory gases by said respiratory gas analyzer, whereby compensation for differential absorption effects of said windows prior to each use is not necessary.

2. An adapter as in claim 1, wherein said windows separate an inside portion of said tubular plastic portion from said infrared transmission and detection means during measurement of said concentration of respiratory gases.

3. An adapter as in claim 1, wherein said positioning means includes means for snap-fitting said airway adapter into said housing means of said respiratory gas analyzer.

4. An adapter as in claim 1, wherein said thin layer of plastic has a thickness of approximately 0.005 inch.

5. An adaptor as in claim 1, wherein said predetermined distance is approximately 0.3 inch.

6. An adaptor as in claim 1, wherein said tubular plastic portion and said thin layer of plastic are formed of at least one of polypropylene and polyethylene.

* * * * *